US008998887B2

(12) United States Patent
Simmen et al.

(10) Patent No.: US 8,998,887 B2
(45) Date of Patent: Apr. 7, 2015

(54) MEDICAL INSTRUMENT HAVING A DETACHABLE HANDLE

(75) Inventors: Markus Simmen, Schwarzenbach (CH); Raphael Spycher, Eschenz (CH); Urs Vogel, Schaffhausen (CH)

(73) Assignee: Karl Storz GmbH & Co. KG (DE)

( * ) Notice: Subject to any disclaimer, the term of this patent is extended or adjusted under 35 U.S.C. 154(b) by 291 days.

(21) Appl. No.: 13/104,661

(22) Filed: May 10, 2011

(65) Prior Publication Data
US 2011/0301577 A1    Dec. 8, 2011

(30) Foreign Application Priority Data

May 10, 2010    (DE) .......................... 10 2010 020 927

(51) Int. Cl.
*A61B 17/00* (2006.01)
*A61B 17/16* (2006.01)
*A61B 17/32* (2006.01)
*A61B 17/29* (2006.01)

(52) U.S. Cl.
CPC .......... *A61B 17/16* (2013.01); *A61B 17/32002* (2013.01); *A61B 17/1622* (2013.01); *A61B 2017/0042* (2013.01); *A61B 2017/0046* (2013.01); *A61B 2017/291* (2013.01); *A61B 2017/2925* (2013.01)

(58) Field of Classification Search
CPC ........ A61B 17/00; A61B 18/18; A61B 17/50; A61B 1/00; A61B 5/00; E21B 15/04; A01B 1/20; F41C 23/00

USPC ........ 173/2; 606/1–14, 205–210, 79; 294/51; 42/72; 600/104, 567
See application file for complete search history.

(56) References Cited

U.S. PATENT DOCUMENTS

| | | | |
|---|---|---|---|
| 5,565,004 A * | 10/1996 | Christoudias | 606/207 |
| 6,277,064 B1 * | 8/2001 | Yoon | 600/114 |
| 6,524,238 B2 | 2/2003 | Velikaris et al. | |
| 6,623,423 B2 * | 9/2003 | Ozaki et al. | 600/104 |
| 7,001,333 B2 | 2/2006 | Hamel et al. | |
| 7,060,039 B2 * | 6/2006 | Voegele | 600/564 |
| 7,328,752 B2 * | 2/2008 | Gass et al. | 173/2 |
| 7,568,304 B1 * | 8/2009 | Moody et al. | 42/72 |
| 7,988,692 B2 * | 8/2011 | Lechot | 606/79 |
| 8,029,510 B2 * | 10/2011 | Hoegerle | 606/80 |
| 8,425,408 B2 * | 4/2013 | Boulais et al. | 600/142 |

(Continued)

FOREIGN PATENT DOCUMENTS

| | | |
|---|---|---|
| DE | 60126977 T2 | 11/2007 |
| WO | 9724072 A1 | 7/1997 |
| WO | 03079911 A1 | 10/2003 |

OTHER PUBLICATIONS

Recess—a space, such as a niche or alcove, set back or indented Collins English Dictionary—Complete and Unabridged © HarperCollins Publishers 1991, 1994, 1998, 2000, 2003.*

*Primary Examiner* — William Thomson
*Assistant Examiner* — Victor Shapiro
(74) *Attorney, Agent, or Firm* — St. Onge Steward Johnston & Reens LLC

(57) ABSTRACT

The invention relates to a medical instrument for removing tissue, in particular a shaver, drill, or morcellator, having a tool that can be set in rotation and a motorized drive for driving the tool, and having an elongate body and a handle that projects laterally from said elongate body. The handle is fastened in a detachable manner to the body.

11 Claims, 4 Drawing Sheets

(56) References Cited

U.S. PATENT DOCUMENTS

| | | |
|---|---|---|
| 2002/0077530 A1 | 6/2002 | Velikaris et al. |
| 2003/0195392 A1 | 10/2003 | Hamel et al. |
| 2005/0134064 A1* | 6/2005 | Nies .............................. 294/51 |
| 2005/0192486 A1 | 9/2005 | Hamel et al. |
| 2007/0244353 A1 | 10/2007 | Larsen |
| 2008/0103413 A1* | 5/2008 | Cicenas et al. ................ 600/567 |
| 2009/0163935 A1 | 6/2009 | McCarthy et al. |
| 2009/0171147 A1* | 7/2009 | Lee et al. ...................... 600/104 |

\* cited by examiner

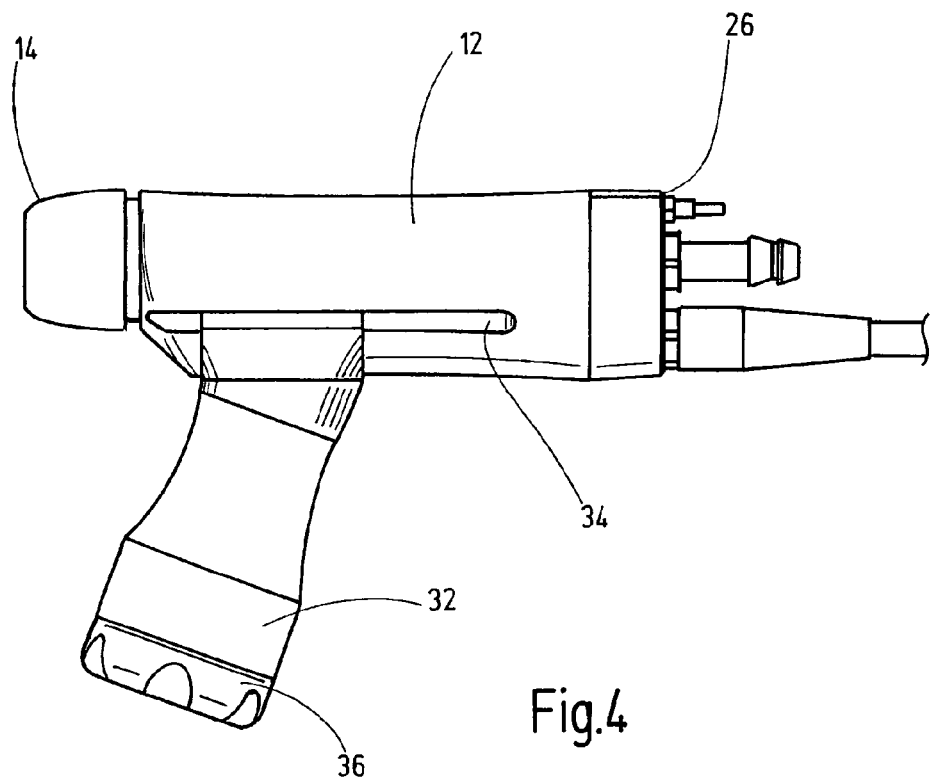
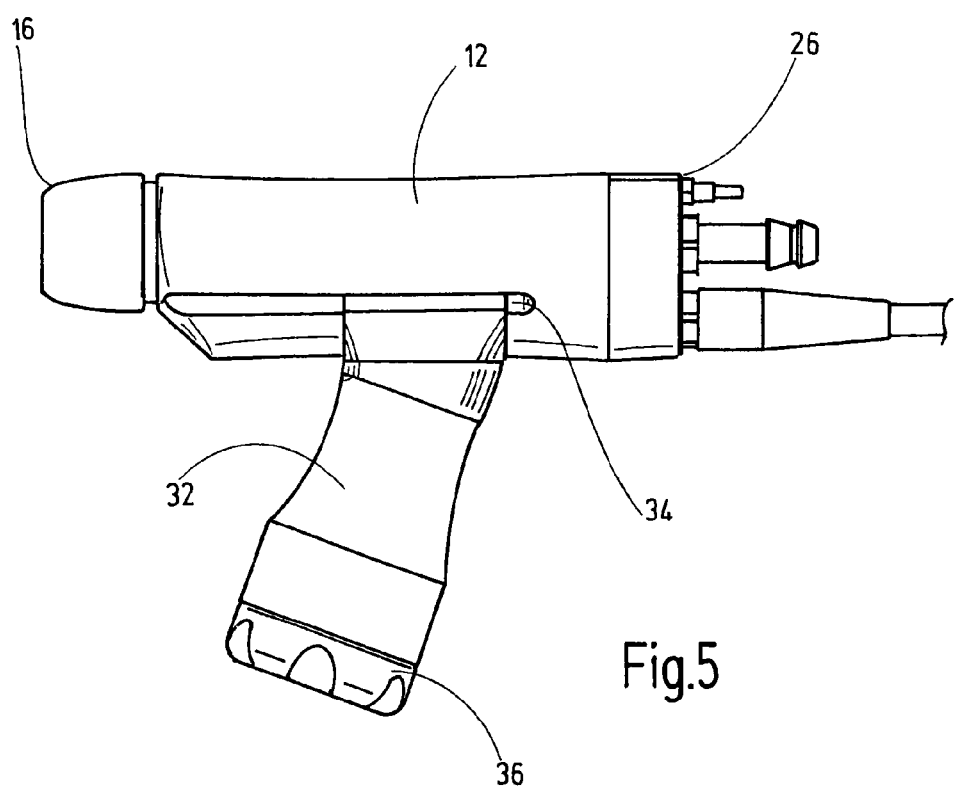

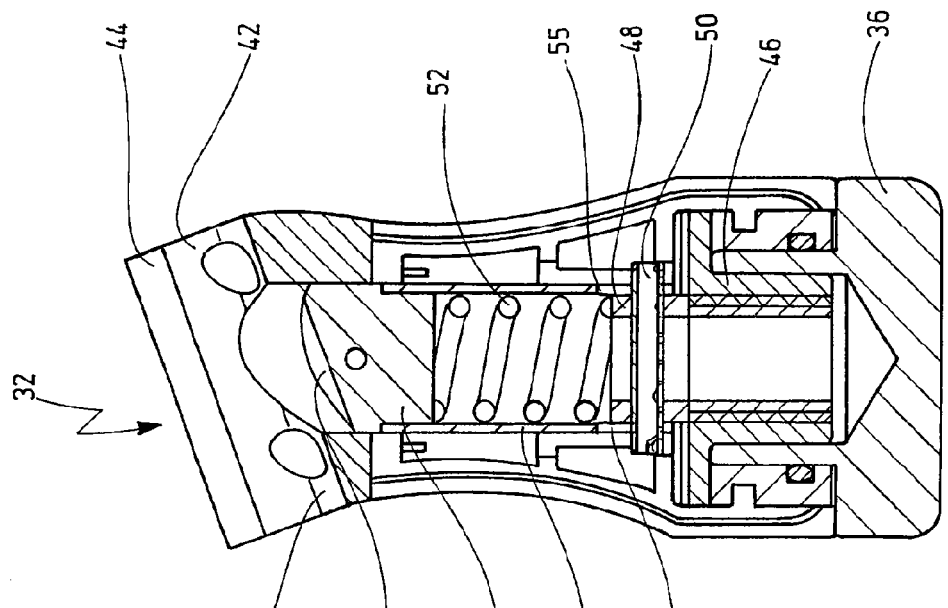
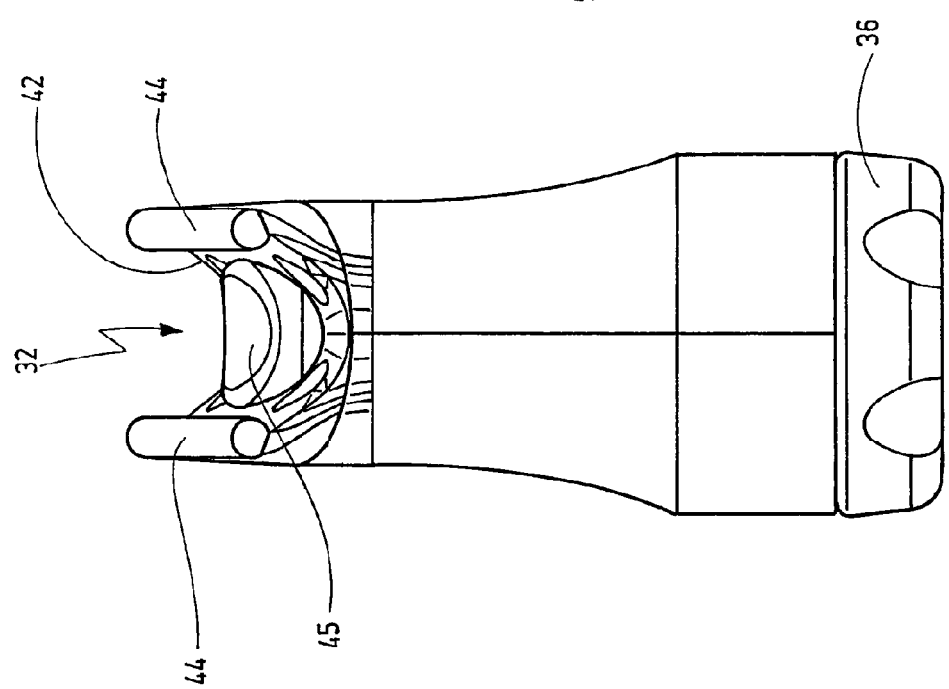

MEDICAL INSTRUMENT HAVING A DETACHABLE HANDLE

CROSS-REFERENCE TO FOREIGN APPLICATION

The present application claims priority of German patent application No. 10 2010 020 927 filed May 10, 2010.

BACKGROUND OF THE INVENTION

The present invention relates to a medical instrument for removing tissue, in particular a shaver, drill, or morcellator, having a tool that can be set in rotation and a motorized drive for driving the tool, the instrument having an elongate body and a handle that projects laterally from said elongate body.

The invention relates further to a handle for use with a medical instrument of the abovementioned kind.

Medical instruments, in particular shavers having an elongate body and a handle that projects laterally from said elongate body, are known and are sold, for example, by the applicant under the designation DrillCut-X. This product is what is known as a shaver for use in ENT medicine. Such instruments are used in minimally invasive surgery to remove tissue from the human or animal body. These instruments usually have an elongate body which has at its distal end a tool that can be set in rotation. The shaver-tool shaft has usually a fixed outer shaft, which generally has a rounded end, and an inner shaft that rotates therein. In the region of its distal end, the outer shaft usually has at least one window having at least one cutting edge. The inner shaft has in this case at its distal end, in the region of the at least one window in the outer shaft, at least one cutting element, which can likewise be designed in the form of a window having a cutting edge. In operation, the inner shaft rotates inside the outer shaft and tissue which enters the window in the outer shaft is then removed between the cutting edge of the window and the rotating cutting elements of the inner shaft and is extracted by suction through the inner shaft, for example by a vacuum being applied. The elongate body of the shaver usually comprises the motor for driving the inner shaft and thus the rotating cutting tool. The laterally projecting handle allows the operator to hold the medical instrument and to manipulate it for the operation.

However, shavers where the motor is arranged in the handle are also known.

In practical operation, it has been shown, however, that a single fixed handle is unfavourable with regard to different use positions of the shaver. It has further been shown that different users prefer different hand positions for using the shaver, with some even dispensing with the handle entirely and tending to hold the elongate body of the shaver, for example in a similar manner to a pen.

The present invention is not limited to shavers, but rather the instrument according to the invention can be for example also a surgical drill or a morcellator. The term "tool" is to be understood as meaning accordingly a drilling tool in the case of a drill, a cutting tool in the case of a shaver or morcellator, and, for example, a milling tool or rasping tool in other instruments for removing tissue.

SUMMARY OF THE INVENTION

It is an object of the invention to describe a medical instrument which, compared with the known instruments, is ergonomically much more flexible and can be adapted to a multiplicity of holding positions.

A further object of the invention is to describe a handle, with the aid of which medical instruments having elongate bodies can be converted for use in a large number of different holding positions.

According to the invention, the object is achieved with regard to the medical instrument mentioned at the beginning in that the handle that projects laterally from the elongate body is fastened in a detachable manner to the body.

The second-mentioned object is achieved further by a handle for use with a medical instrument for removing tissue, in particular a shaver, drill, or morcellator, which has a tool that can be set in rotation, a motorized drive for driving the tool and an elongate body, wherein the handle has on its upper side a recess for accommodating the body of the medical instrument, wherein at least two substantially parallel bars which are located opposite one another are provided in the upper region of the recess and, in a state in which the handle is connected to the medical instrument, engage in corresponding grooves that are arranged on the body.

In this way, an instrument is created, in which the laterally projecting handle can be detached or attached, so that, depending on the preferred holding position, the instrument can be held via the laterally projecting handle or, for example, in the manner of a rod. Furthermore, by way of the handle, already existing medical instruments having an elongate body can be equipped with a laterally projecting handle.

The term "bars", as is used in the present application, and as are provided in the upper region of the recess in the handle according to the invention, describes any structure which is capable of engaging in corresponding grooves and achieving guided mounting of the medical instrument. These bars can have any length, with it being possible in the extreme case for them to be reduced to pins and in the other extreme case for them to extend over the entire length of the recess. It is also possible for the bars to be composed of a plurality of smaller individual bars.

In one embodiment of the invention, the handle can be fixed to the body at different positions along the longitudinal axis. In particular, the handle can be fixed in a stepless manner at different positions along the longitudinal axis of the body.

This measure further increases the ergonomic flexibility of the medical instrument according to the invention, since as a result, an operator can set positions of the handle more specifically with regard to the operative conditions and to his personal preferences. Furthermore, the instrument can as a result be used easily by different operators who have different preferences or, for example, different-sized hands.

In one embodiment of the abovementioned measure, the handle comprises a locking system, by way of which it can be locked in a position along the longitudinal axis of the body.

Even though it is possible to fix the handle at different positions along the longitudinal axis of the body in other ways than by way of a locking system, it is advantageous to provide a locking system because when the locking system is opened, the handle can be removed easily from the medical device, and when the locking system is closed, the handle is reliably protected against slipping out of the fixed position. This embodiment also contributes to the operational reliability of the instrument, this being important since the instrument is one which is used to remove tissue rapidly and therefore always has to be under control. Also, the handle has to be seated firmly on the instrument in the case of vibrations which may be caused by the motorized drive.

Locking can in this case take place in any manner known to a person skilled in the art, depending on whether it takes place in steps or in a stepless manner. Possibilities for locking systems are spring-loaded pin locks or ball locks which engage in blind holes, latching noses, or locking systems in which, for example, the bars are pressed in any way against the instrument or the instrument is pressed against the bars.

In order to attach the handle to the body of the instrument, it may have a recess which is closed all or part of the way round and in which the body is accommodated.

In a preferred embodiment, the handle of the medical instrument has a recess for accommodating the body, wherein at least two substantially parallel bars which are located opposite one another are provided in the upper region of the recess and, in the state in which the handle is connected to the medical device, engage in corresponding grooves that are arranged on the body.

This embodiment has the advantage that it is structurally simple, allows the position of the handle to be changed steplessly, but at the same time ensures that the body of the medical instrument is guided reliably and securely on the handle.

In one embodiment of the abovementioned measure, the handle further has at least one adjustable finger, which, from a position in which a tip of the finger is recessed in an inner surface of the recess, can be braced against the body in order to lock the handle to the body, or from which the finger can be moved in the direction of the interior of the recess.

In this embodiment, locking is achieved as follows. In a first step, the medical instrument is pushed into the handle, with the finger being located in the recessed position and with the bars of the handle engaging in grooves provided on the instrument. In a second step, the finger is pressed against the body of the instrument, so that the instrument is now pressed substantially from below against the bars. It has been shown that this structure both allows easy locking and unlocking of the handle and also leads to particularly reliable and secure locking.

In a further embodiment of the invention, the handle projects from the body at an angle other than 90° or between the longitudinal axis of the recess and the longitudinal axis of the handle there is an angle other than 90°.

It has been shown that handles which project from the elongate body at an angle other than 90° are frequently perceived as being ergonomically more comfortable by the user.

In one embodiment of the abovementioned measure, the handle is designed in such a way that it can be attached to the body in a manner angled in either the distal direction or the proximal direction.

This means that, with regard to a line that is at right angles to the longitudinal axis of the elongate body, the handle is deflected either to the front or to the rear. On account of the fact that the handle is designed such that it can be attached to the body in a manner deflected in either direction, the ergonomic flexibility is further increased and the medical instrument can be adapted, for example, to a more upwardly or more downwardly oriented working angle.

It goes without saying that the features mentioned above and those still to be mentioned below can be used not only in the combination stated in each case, but also in other combinations or on their own, without departing from the scope of the present invention.

The invention is explained and described in more detail in the following text on the basis of selected exemplary embodiments in conjunction with the drawings, in which:

BRIEF DESCRIPTION OF THE DRAWINGS

FIG. 4 shows a third configuration of the medical instrument from FIG. 1;

FIG. 5 shows a fourth configuration of the medical instrument from FIG. 1;

FIG. 6 shows an end view of a handle for use with a medical instrument; and

FIG. 7 shows a side view of the handle from FIG. 6 in section.

DETAILED DESCRIPTION OF PREFERRED EXEMPLARY EMBODIMENTS

Figure 1:
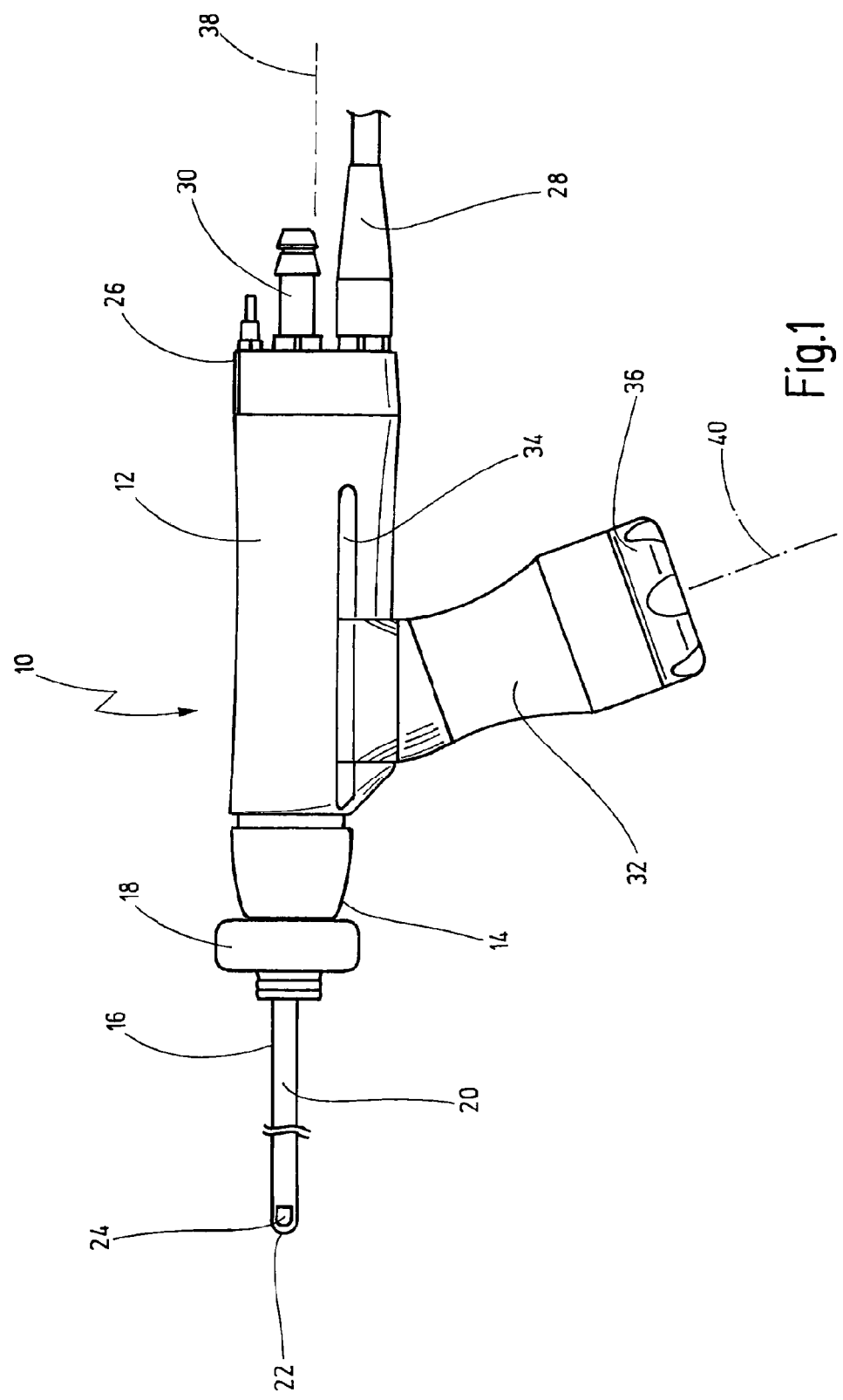
FIG. 1 shows a side view of a medical instrument in the form of a shaver.

In FIG. 1, a medical instrument in its entirety is designated by the reference numeral 10.

Without restricting generality, the medical instrument 10 is a shaver. This shaver has an elongate body 12, with a shaver tool shaft 16 being arranged at its distal end 14.

The shaver tool shaft 16 has a coupling 18 for coupling to the body 12 of the shaver, and also an outer shaft 20 which ends at its distal end in a rounded end 22. Furthermore, a window 24 is provided in the region of the distal end of the outer shaft 20, said window 24 being equipped with cutting edges and forming a part of the cutting tool of the shaver.

Provided at the proximal end 26 of the body 12 are connections 28 and 30. The connection 28 is a power connection which supplies an electric motor, which is arranged in the body 12 and is not illustrated here, with power. This electric motor sets an inner shaft, which is arranged inside the outer shaft 20 of the tool shaft 16 and is not illustrated here, in rotation. The rotation of the inner shaft with respect to the fixed outer shaft 20 of the tool then leads to the desired cutting action, since the inner shaft is provided with cutting edges in the region of the window 24.

The connection 30 at the proximal end 26 of the body 12 serves to apply a vacuum to the inside of the tool shaft 16, so that pieces of tissue removed by the cutting action are extracted by suction from the instrument through the elongate body 12.

Arranged on the underside of the elongate body 12 is a handle 32. The handle 32 is arranged in this case in that bars provided on the handle 32 engage in a groove 34 in the body 12 of the medical instrument 10. The handle 32 has at its lower end a rotary knob 36, which serves to lock the handle 32 to the body 12 of the medical instrument 10. The functioning of the handle 32 will be described in more detail on the basis of an individual handle in FIGS. 6 and 7.

In the configurations illustrated, the handle 32 is angled in the direction of the proximal end 26 of the body 12, i.e. the angle between the longitudinal axis of the body 12, said axis being illustrated here by a dashed line 38, and the longitudinal axis of the handle 32, said axis being illustrated by a dot-dash line 40, is other than 90°.

On account of the fact that the connection between the handle 32 and the body 12 is designed in the form of bars and grooves 34, the handle 32 can be fixed steplessly at different positions along the longitudinal axis of the body 12. Since the grooves 34 in the body 12 are furthermore open in the direction of the distal end 14 of the body 12, the handle 32 can also be removed completely from the body 12, so that the shaver can then be held, for example in the manner of a rod. It is also possible to rotate the handle 32 through 180° and to reattach it to the body 12 in the opposite orientation. In this case, the handle 32 would be angled in the direction of the distal end 14 of the body 12.

Various configurations which can be achieved in this way are illustrated in FIGS. 2 to 5, with the shaver tool shaft 16 not being illustrated in FIGS. 2 to 5 for reasons of simplicity.

Figure 2:
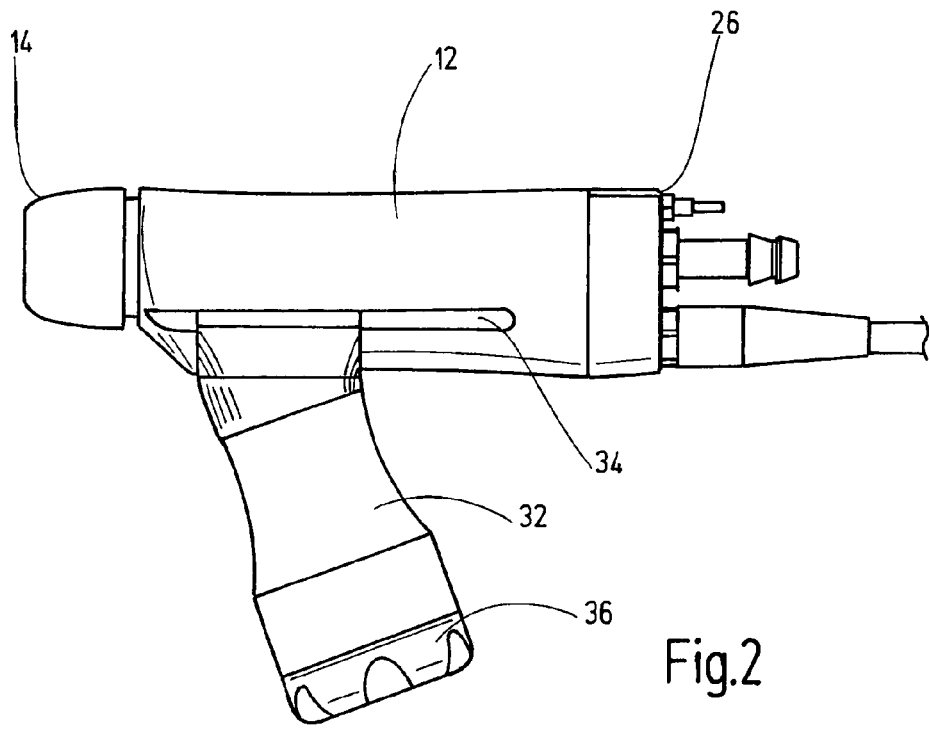
FIG. 2 shows a first configuration of the medical instrument from FIG. 1.

The configuration illustrated in FIG. 2 corresponds to that of FIG. 1.

Figure 3:
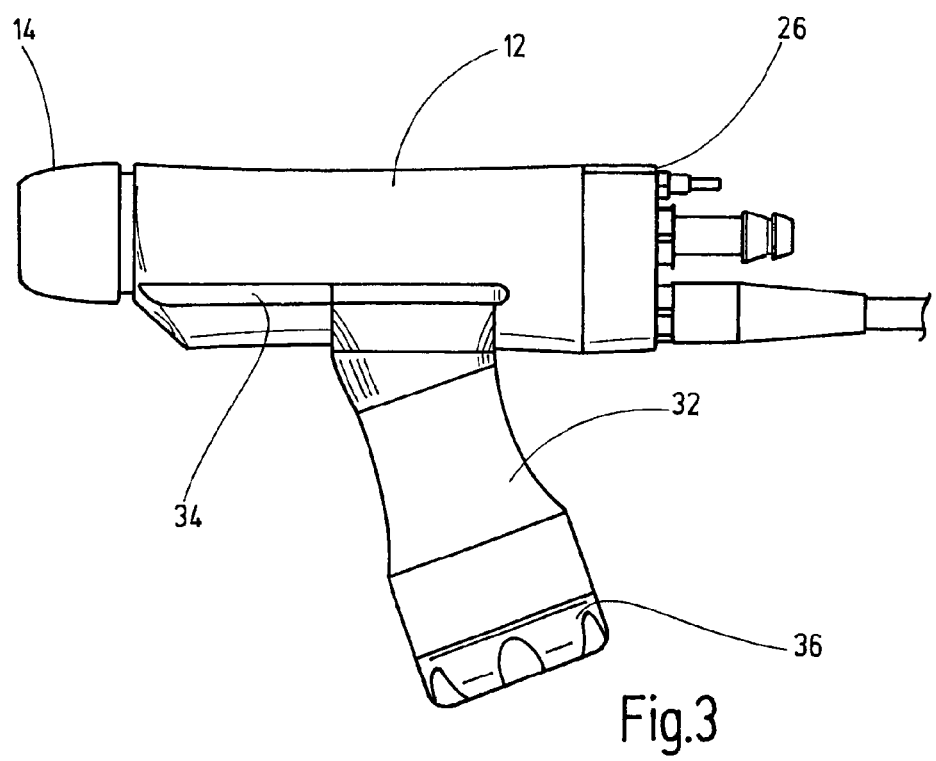
FIG. 3 shows a second configuration of the medical instrument from FIG. 1.

The configuration illustrated in FIG. 3 differs from the configuration illustrated in FIG. 2 in that the handle has been displaced in the direction of the proximal end 26 of the body 12 compared with FIG. 2. In order to move the handle into this position, the locking system has to be released merely by the rotary knob 36 being rotated, and then the handle 32 has to be displaced along the groove 34 in the direction of the proximal end 26 of the body 12. Once the handle 32 has reached the desired position, the rotary knob 36 is rotated in the opposite direction and the handle 32 is locked to the body 12 again.

The configuration illustrated in FIG. 4 differs from the configuration illustrated in FIG. 2 in that the handle 32 is no longer angled in the direction of the proximal end 26 of the body 12, but is now angled in the direction of the distal end 14 of the body 12. Such a position is for example useful when the medical instrument is intended to be inclined downwards. In order to reach this position, again the locking system of the handle 32 is released by rotation of the rotary knob 36 and said handle 32 is pulled out of the grooves by the handle 32 being moved in the direction of the distal end 14 of the body 12. The handle is then rotated through 180° and reinserted into the grooves 34 in the body 12 and moved in the direction of the proximal end 26 of the body 12 until it reaches the desired position. The handle 32 is then locked on the body 12 again by the rotary knob 36 being rotated in the opposite direction.

The configuration illustrated in FIG. 5 differs from the configuration illustrated in FIG. 4 in that the handle 32 has again been displaced in the direction of the proximal end 26 of the body 12. In order to reach this configuration, the locking system of the handle 32 to the body 12 is again released by the rotary knob 36 being rotated and the handle 32 is moved in the grooves 34 in the body 12 in the direction of the proximal end 26 of the body 12. Once the handle 32 has reached the desired position, the handle 32 is again locked to the body 12 by the rotary knob 36 being rotated in the other direction.

FIG. 6 now shows on its own a handle for use with a medical instrument for removing tissue. This handle corresponds substantially to the handle illustrated in FIGS. 1 to 5 in conjunction with the medical instrument 10, and so the same reference numerals are used for the same components that have already been described.

In FIG. 6, a handle for a medical instrument is designated as a whole by the reference numeral 32. The handle 32 has at its upper end a recess 42 which is designed such that it can receive the medical instrument(s) with which the handle is intended to be used.

Arranged in the upper region of the recess 42 are two opposing and substantially parallel bars 44. In the present case, the bars 44 are arranged at the upper end of the recess 42. However, they can also easily be arranged at positions further down in the recess 42, as long as this does not impair the connection between the medical instrument and the handle 32.

Also visible in this illustration is a tip 45 of a finger 54, which is illustrated here in an extended position, with this position not being reached, however, in the case that the handle is arranged on a medical instrument, as will be described below. The finger 54 serves, when the handle is fixed on the instrument, to press against the body 12 and to press the latter accordingly against the bars 44, this leading to the locking of the handle 32 to the instrument.

FIG. 7 illustrates a section view of the handle 32 illustrated in FIG. 6. It is apparent from this illustration that the inside of the rotary knob 36, which is arranged at the lower end of the handle, is connected to an internal thread 46. This internal thread 46 engages in the external thread of a displacement bolt 48. The displacement bolt 48 furthermore has a guide bolt 50. If the rotary knob 36 is now rotated, then the displacement bolt 48, on account of the fact that the guide bolt 50 is guided, cannot follow this rotary movement and therefore does carry out a translational movement along the longitudinal axis of the handle. The displacement bolt 48 interacts with a spring 52, which is supported against the finger 54. A sleeve 51, which surrounds the spring 52, is connected to the finger 54. The sleeve 51 has a slot-like recess 53 into which the guide bolt 50, which can move in relation to the sleeve 51, engages.

If the handle 32 is now mounted on a body, for example the body 12 of the instrument 10, the finger 54 is located in its set-back position, illustrated in FIG. 7, with respect to the recess 42. In this position, the tip 45 of the finger 54 is recessed in an inner surface 43 of the recess 42. From this position, the finger 54 can be moved in the direction of the interior of the recess 42. Once the bars 44 have been inserted into corresponding grooves in the body of the instrument, to which the handle 32 is intended to be fixed, the rotary knob 36 is rotated until the finger 54 touches the body of the instrument. However, when it touches it, the finger 54 does not yet exert any force on the body of the instrument. The rotary knob 36 is now rotated further in the same direction, as a result of which the guide bolt 50 moves into the slot-like recess 53 in the sleeve 51 in relation to the latter. At the same time, the displacement bolt 48 is moved against the spring 52, as a result of which the latter is slowly tensioned. Since the sleeve 51, on account of its secure connection to the finger 54 and because the finger 54 is resting against the body of the instrument, can no longer move in the direction of the body of the instrument, one end 55 of the recess 53 forms a stop for the guide bolt 50. The tensioning of the spring 52 and thus the increase in the force of the finger 54 on the body of the instrument are thus limited by this stop. The handle 32 is now locked to the body of the instrument.

The handle 32 is detached from the instrument in a corresponding manner in the opposite manner, it being necessary merely to rotate the rotary knob 36 in the opposite direction until the finger 54 disengages from the body of the instrument, after which the handle 32 can be detached from the instrument.

What is claimed is:

1. A medical instrument for removing tissue comprising:
   an elongate body,
   a tool shaft coupled to a distal end of said elongate body, said tool shaft being rotatable,
   a motorized drive for rotating said tool shaft, said motorized drive being housed in said elongate body and connected to a power connection,
   a connection being coupled to a proximate end of said elongate body, said connection being configured for supplying a vacuum to the inside of said tool shaft; said tool shaft being configured for removing said tissue by suction;
   a handle projecting laterally from said elongate body, when mounted at said elongate body said handle being a separable component and not a part of said elongate body, wherein said handle is fastened in a detachable manner to said body, and wherein said elongate body is shaped in that it can be ergonomically gripped in the manner of a rod when said handle is detached, said tool shaft can be rotated by said motorized drive when said handle is detached.

2. The medical instrument of claim 1, wherein said handle can be fixed to said body at different positions along a longitudinal axis of said body.

3. The medical instrument of claim 2, wherein said handle can be fixed in a stepless manner at different positions along said longitudinal axis of said body.

4. The medical instrument of claim 2, wherein said handle has a locking system, by way of which it can be locked in a position along said longitudinal axis of said body.

5. The medical instrument of claim 1, wherein said handle has a recess for accommodating said body, wherein at least two substantially parallel bars which are located opposite one another are provided in an upper region of said recess and, in a state in which said handle is connected to said medical instrument, engage in corresponding grooves that are arranged on said body.

6. The medical instrument of claim 5, wherein said handle further has at least one adjustable finger, which, from a position in which a tip of said finger is recessed in an inner surface of said recess, can be braced against said body in order to lock said handle to said body.

7. The medical instrument of claim 1, wherein said handle projects from said body at an angle other than 90°.

8. The medical instrument of claim 7, wherein said handle is designed in such a way that it can be attached to said body in a manner angled in either a distal direction or a proximal direction.

9. A handle for use with a medical instrument comprising:
on its upper side a recess for accommodating the body of said medical instrument, wherein at least two substantially parallel bars which are located opposite one another are provided in an upper region of the recess and, in a state in which said handle is connected to said medical instrument, engage in corresponding grooves that are arranged on said body of said medical instrument;
wherein said handle further has at least one adjustable finger, which, from a position in which a tip of said finger is recessed in an inner surface of said recess, is movable in the direction of an interior of said recess, and
wherein a rotary knob is connected to said adjustable finger, a rotation of said rotary knob moves said finger in said direction of said interior of said recess, said rotation of said rotary knob allows the control of a force exerted by said finger onto said body of said medical instrument.

10. The handle of claim 9, wherein between a longitudinal axis of said recess and a longitudinal axis of said handle there is an angle other than 90°.

11. The handle of claim 10, wherein said handle can be attached to said body in a manner angled in either a distal direction or a proximal direction.

* * * * *